(12) United States Patent
Annis

(10) Patent No.: US 7,620,150 B1
(45) Date of Patent: Nov. 17, 2009

(54) X-RAY BACKSCATTER SYSTEM FOR IMAGING AT SHALLOW DEPTHS

(76) Inventor: Martin Annis, 67 Banks St., Cambridge, MA (US) 02138

(*) Notice: Subject to any disclaimer, the term of this patent is extended or adjusted under 35 U.S.C. 154(b) by 0 days.

(21) Appl. No.: 12/022,751

(22) Filed: Jan. 30, 2008

Related U.S. Application Data

(63) Continuation-in-part of application No. 11/838,783, filed on Aug. 14, 2007, now Pat. No. 7,561,666.

(60) Provisional application No. 60/898,232, filed on Jan. 30, 2007.

(51) Int. Cl.
*G01N 23/203* (2006.01)
(52) U.S. Cl. .................................................. 378/87
(58) Field of Classification Search ............... 378/86, 378/87, 88, 89

See application file for complete search history.

(56) References Cited

U.S. PATENT DOCUMENTS

| | | | |
|---|---|---|---|
| 5,692,029 A * | 11/1997 | Husseiny et al. | 378/88 |
| 2004/0028178 A1 * | 2/2004 | Jupp et al. | 378/64 |
| 2007/0098142 A1 * | 5/2007 | Rothschild et al. | 378/57 |

* cited by examiner

*Primary Examiner*—Chih-Cheng G Kao
(74) *Attorney, Agent, or Firm*—Steven K Martin; Altman & Martin

(57) ABSTRACT

The apparatus has an x-ray source that emits an x-ray cone beam through a tubular, x-ray-blocking guide to a planar template with a small pinhole to produce a pencil beam. The template is movable so the pencil beam can scan the target region to be imaged. Between the template and target region is an x-ray detector assembly with a plastic scintillator. The scintillator has an opening about the same size and shape as the target region that allows the pencil beam to pass to the target region. Photo-multiplier detectors receive the light generated by the backscattered x-rays in the scintillator. The method of the present invention employs the apparatus. Multiple x-rays source locations permit the generation of 3D images.

19 Claims, 7 Drawing Sheets

X-RAY BACKSCATTER SYSTEM FOR IMAGING AT SHALLOW DEPTHS

CROSS-REFERENCES TO RELATED APPLICATIONS

The present application is a continuation-in-part application of application Ser. No. 11/838,783, filed Aug. 14, 2007 for PERSONNEL X-RAY INSPECTION SYSTEM in the name of Martin Annis, which claims the benefit of U.S. Provisional Patent Application No. 60/837,838, filed Aug. 15, 2006 for BACKSCATTER PERSONNEL SYSTEM in the name of Martin Annis, and U.S. Provisional Patent Application No. 60/875,630, filed Dec. 19, 2006 for METHOD TO USE A DUAL ENERGY X-RAY SOURCE IN A BACKSCATTER BODY SCAN SYSTEM in the name of Martin Annis. The further applicant wishes to claim the benefit of U.S. Provisional Patent Application No. 60/898,232, filed Jan. 30, 2007 for METHOD TO USE A DUAL ENERGY X-RAY SOURCE IN A BACKSCATTER SYSTEM FOR DERMATOLOGY AND MAMMOGRAPHY in the name of Martin Annis.

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to medical diagnostic systems, more particularly, to diagnostic instruments for detection of tumors of the skin.

2. Description of the Related Art

The incidence of skin cancer is growing rapidly. This is possibly due to the loss of ozone in the upper atmosphere. These cancers can be successfully treated if they are discovered early. It is recommended that people see their dermatologists yearly, so the number of examinations is very large and the time and expense is correspondingly large. At the present time, dermatologists are limited in the tools that can be used for the yearly examinations of patients. The examination is usually a visual and tactile examination of all of the surface lesions of the patient's body using a magnifying glass. Since the larger portion of a tumor is below the surface of the skin, it would be very useful to have a means of observing the volume of tissue just below the observed lesion on the surface of the skin, to a depth of about a centimeter.

Current x-ray procedures for examining the region of the body just below the surface of the body utilize transmission x-ray systems. These systems must penetrate the entire width of the body that lies below the region of interest just below the skin lesion. In order to do this, the peak energy of the x-ray spectrum must be sufficiently high to penetrate the body and the x-ray exposure to the patient is correspondingly high. In addition, the contrast in observing small differences in the density in the soft tissue is not sufficiently great to make such an x-ray examination useful.

BRIEF SUMMARY OF THE INVENTION

The purpose of this invention is to provide a system to examine the region below suspicious lesions on the surface of the skin. It is important that the system be of low radiation exposure to the healthy tissue deep within the body. This is accomplished in the current invention by using backscattered x-rays that expose only a relatively small volume of the patient's body. The system is also compact and inexpensive, which is desirable given the large number of patients that must be served in doctor's offices.

The present invention has a number of potential applications: 1. It can be used to inspect breasts of patients who are have been seen by mammography to have suspicious regions of the breast. These regions can be inspected in detail and 3D images can be obtained to better identify and diagnose the problem. 2. The present invention can be used to image the region below lesions on the surface of the skin. At the present time, there are no inexpensive methods of doing this. Having a backscatter and/or a 3D backscatter image of this region, will allow physicians to have this information quickly and inexpensively. 3. There are a large number of aging aircraft throughout the world. A common problem in these aircraft is cracks, typically found around rivets. The present invention allows rapid inspection of the region below the surface of the airplane of the aircraft skin. A 3D image of this region of the skin will allow repair of these fatigue cracks in the aircraft skin. 4. There are numerous other applications in industry and medicine which share the attribute of being available only from one side and the present invention may be employed in all of these applications.

The apparatus of the present invention has an x-ray source that emits an x-ray cone beam into a tubular, x-ray-blocking guide. At the other end of the guide is a planar template with a small pinhole. The template blocks x-rays that do not impinge on the pinhole and the pinhole allows those impinging x-rays through as a pencil beam. The template is movable in the two dimensions in the plane of the template so the pencil beam can scan the target region to be imaged. On the other side of the template is an x-ray detector assembly that includes a plastic scintillator that is parallel to the template. The scintillator has an opening that allows the pencil beam to enter the target region without penetrating the scintillator, but is small enough to collect a large fraction of the backscattered x-rays from the target. Optionally, the plastic scintillator will move with the template in the case where the target region is larger than about 2.5 cm×2.5 cm. Photo-multiplier detectors receive the light generated by the backscattered x-rays in the scintillator.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION OF THE INVENTION

The use of backscatter x-ray systems for the inspection of personnel for security purposes is now common. These systems operate at very low exposure levels and are limited to an exposure of 10 micro-Roentgens (μR) by government regulation. With the superior intrinsic imaging efficiency of backscatter near the surface of an object, it is possible to see detail of tumors that have never before been seen. For the first time, the soft tissue can be imaged in x-rays with a contrast an order of magnitude or more better with the system of the present invention than with previous systems in the region close to the surface of the soft tissue.

Figure 1:
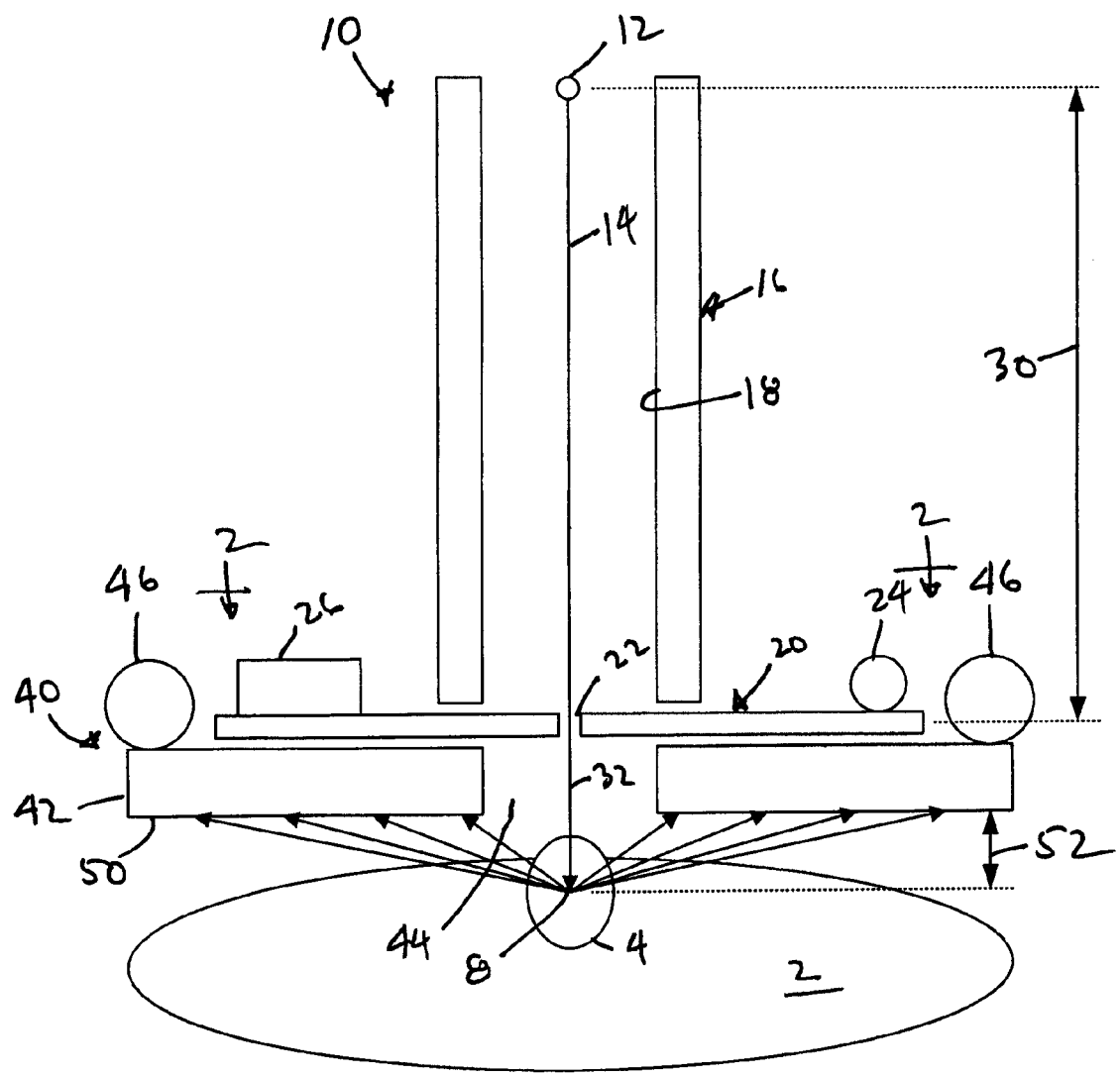
FIG. 1 is a schematic side view of an embodiment of the present invention.
Figure 2:
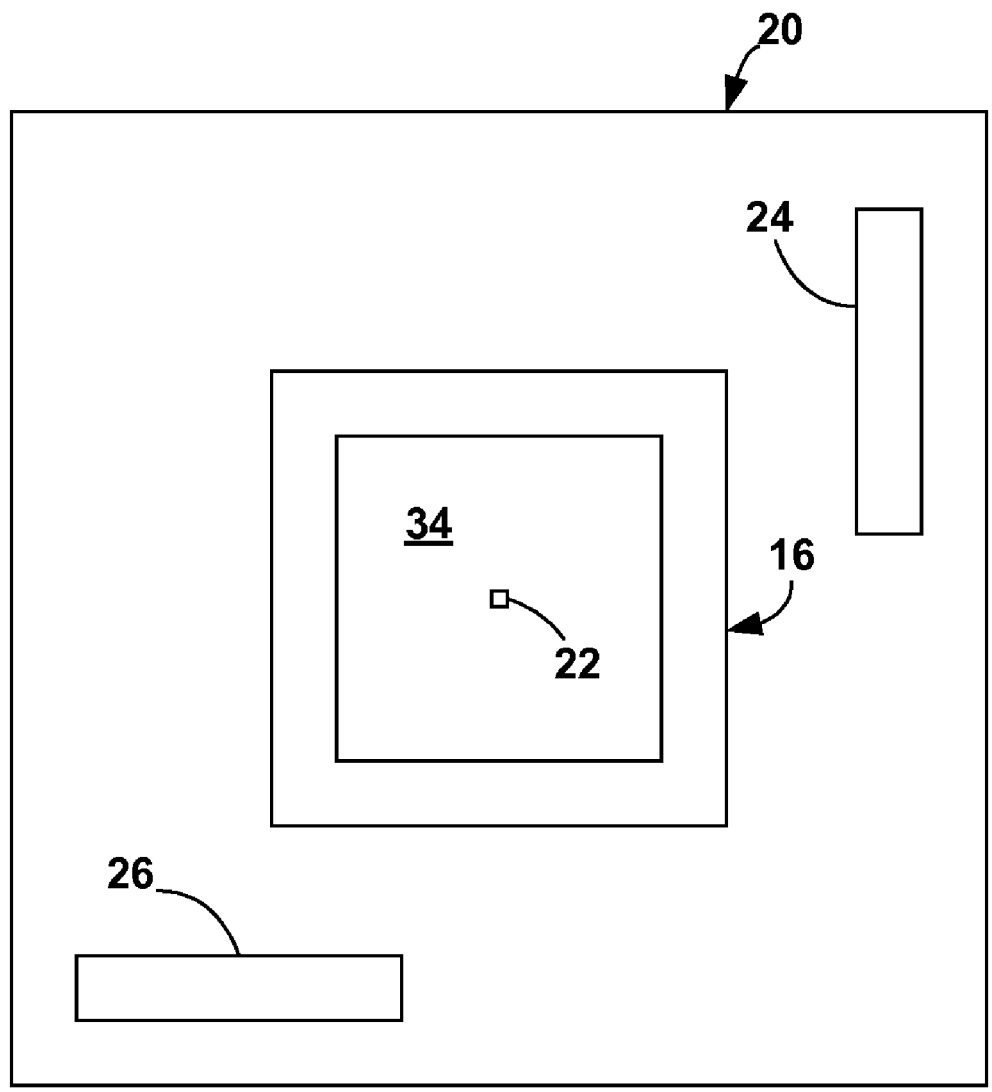
FIG. 2 is a schematic view of the x-ray beam outlet of the embodiment of FIG. 1 taken along the line 2-2.

The system 10 of the present invention is shown in the FIGS. 1 and 2. An x-ray source 12 emits an x-ray cone beam 14 into a tubular guide 16 with an x-ray blocking wall 18, such as lead. At the other end of the guide 16 is a planar template 20 with a small pinhole 22. The cross-sectional area of the guide 16 approximately represents the size of the object target region to be imaged. The size of the pinhole 22 can range from approximately 0.01 $mm^2$ to approximately 4 $mm^2$, and the size and shape are described in more detail below. The template 20 is composed of a material, such as tungsten, that blocks x-rays that do not impinge on the pinhole 22 and the pinhole 22 allows those impinging x-rays through as a pencil beam 32. The distance 30 from the x-ray source 12 to the plane of the template 20 can be in the range of from about 2.5 cm to about 30 cm and is typically about 15 cm. The template 20 is movable in the two dimensions, x and y, in the plane of the template 20 via two precision stepping or servo motors 24, 26, as described below.

On the other side of the template 20 is an x-ray detector assembly 40. The detector assembly 40 includes a plastic scintillator 42 that has a thickness in the range of from about 0.5 mm to about 3 cm and is typically about 1 or 2 cm thick. The scintillator may also be a conventional sheet as used in medical radiography. The scintillator 42 is parallel to the template. In one embodiment, the scintillator 42 is fixed relative to the x-ray source 12. The scintillator 42 has an opening 44 to allow the pencil beam 32 emitted from the pinhole 22 to pass directly to the target region without penetrating the scintillator. The opening 44 is large enough to cover the target region but small enough to permit the scintillator 42 to collect a large fraction of the backscattered x-rays from the target region. In another embodiment, the scintillator, rather than being fixed relative to the x-ray source 12, is fixed relative to the template 20 so that it moves with the template in the case where the target region is relatively large, for example larger than about 2.5 cm×2.5 cm. The opening 44 is slightly larger than the pinhole 22 so that the scintillator 42 can collect a large fraction of the backscattered x-rays from the target region. Photo-multiplier detectors 46 at the surface of the scintillator 42 receive the light generated in the scintillator 42 by the backscattered x-rays 48. The receiving surface 50 of the scintillator 42 should be as adjacent to all of the volume of the target region 8 as practical. Thus, the system is effective for approximately 3 cm below the surface.

The size of the target area may be as large as 20 cm across and still allow a major increase in flux over the prior art. Other dimensions, including the pinhole size and the x-ray source to pinhole distance can be increased appropriately. The key element is that the pinhole and backscatter detector distance to the object is as small as possible.

The system 10 is very small because the region to be inspected is small, less than an inch across in the application for dermatology. Thus, a unique feature of the invention is its dramatically smaller size which allows the use of a very low power x-ray source 12. Indeed, without the uniquely small dimensions, the system 10 would be prohibitively expensive for this dermatology application.

Previous backscatter inspection systems for security inspection of personnel operate at 10 micro-Roentgens, a distance of about 80 cm from the source to the body and a body area to be inspected of 45×200 cm. In the present design, the smaller dimensions provide a factor of about $80^2/15^2=28$ increase in x-ray flux due to the smaller distance from the x-ray source 12 to the surface of the skin 2 than is possible in the prior art systems. In addition, the smaller area that must be scanned by the pencil beam 32 is about 2.5 cm×2.5 cm=6.25 $cm^2$, compared to about 45 cm×200 cm=9000 $cm^2$ for the surface area of a total body scan. Thus, the x-ray source strength required to produce the required contrast in the images can be easily achieved with a pinhole 22 width of 1 mm and pixel size of 0.5 mm, as described below. A pixel size smaller than the pinhole width is achieved by application of the Nyquist Theorem.

The ability to detect tumor tissue depends on two things:

1. The separation of normal soft tissue and tumor soft tissue is determined by the mass absorption coefficients of the two materials. If tumor tissue has the same elemental composition as normal tissue, the separation of the two materials is only in the density of the materials. On the other hand, if tumor tissue has a higher concentration of calcium than normal tissue, the measured separation of the materials will be much larger. This separation is not determined by the parameters of the system including the incident flux; it is determined by the density and mass absorption coefficients of the normal and tumor tissue. The separation between normal tissue and tumor tissue is typically about 1% in contrast.

2. To observe the separation of the two kinds of tissue, tumor and normal, there must be a sufficient number of x-ray photons per backscattered pixel to establish a standard deviation in the number of photons detected that is small compared to the separation as defined in #1, above.

The template 20 is moved by the motors 24, 26 to scan the pinhole 22 across the entire area of the guide cross-section, an area of approximately 2.5 cm×2.5 cm or 6.25 $cm^2$, shown at 34 in FIG. 2. In the x direction, the x motor 24 moves the template 20 rapidly back and forth. In the y direction, the y motor 26 moves the template 20 much more slowly, so the pinhole 22 has only translated by one width in the y direction while it moves 2.5 cm in the x direction. Thus, a raster scan of the entire region to be examined is accomplished. The present invention contemplates that any mechanism known in the art can be used to move the template.

Assuming that the pinhole 22 is either round with a 1 mm diameter or square with 1 mm on a side, if the 2.5 cm×2.5 cm scan is completed in 2 seconds and the pixel size is 0.5 mm, the number of pixels in each of the x direction and the y direction is 25/0.5=50, for a total of 50×50~2500 pixels. The sample time per pixel is therefore 2/2500=0.8 ms.

Tumors occur mostly in regions where the skin is exposed to the UV from the sun. Most of these regions have a relatively thin coating of soft tissue that is underlain by bone. Since bone absorbs x-rays far more than soft tissue, backscatter from the patient is limited to about 2 cm of soft tissue. It is therefore possible to restrict the depth of detection to 2 cm. It is also possible to limit the peak energy of the source to 30 keV, although the case of 70 keV is also calculated throughout the present specification. Multiple peak x-ray energies may be used to produce x-ray images at these energies of the same target. A comparison of these images at different peak x-ray energies allows the determination of the local composition and density of the material in the target. The present invention has application for x-ray peak energies from 10 keV up to 500 keV. Also, the mass absorption coefficient for the x-rays that are incident are used as well as those that backscatter.

The performance of a pencil beam backscatter system that utilizes a moving pinhole collimator is calculated below. The system is optimized to allow the most efficient use of the x-rays emitted by the source. The calculation assumes parameters that can be simply changed from the chosen ones in order to optimize the design.

The mass absorption coefficients are taken from the National Institute for Standards and Technology (NIST) and are shown in Table I.

TABLE I

| Energy Coef (keV) | Attenuation Coef $\mu/\rho$ (cm$^2$/g) | Absorption $\mu/\rho$en (cm$^2$/g) |
| --- | --- | --- |
| 10 | 5.38 | 4.99 |
| 15 | 1.70 | 1.40 |
| 20 | 0.823 | 0.566 |
| 30 | 0.379 | 0.162 |
| 40 | 0.269 | 0.072 |
| 50 | 0.226 | 0.043 |
| 60 | 0.205 | 0.033 |
| 80 | 0.182 | 0.026 |
| 100 | 0.169 | 0.025 |

The following parameters are chosen to illustrate the invention. They may be changed without changing the thrust of the invention. A skin entrance exposure of less than 7 mR (0.6 mGy) has been assumed, which is less than the exposure of a chest x-ray. The peak x-ray energy has been taken to be 30 keV and 70 keV. The cross-sectional dimension of the scanning x-ray pencil beam is assumed to be 1 mm×1 mm. Double sampling in both directions by using the Nyquist Theorem, results in a spatial resolution, or pixel size, of 0.5 mm. Further, Z is the atomic number of the low Z elements that form human tissue, W is the atomic weight of an element (g/atomic weight), Y=½ is the ratio Z/W and is constant for these low Z elements, $\mu e$ is the cross-section per electron for all elements for backscattering (cm$^2$/electron), 6×10$^{23}$ is Avogadro's number (atoms/atomic weight), Ne=Y×A is the number of electrons/g for each material, Dpix=0.05 cm is the length of a side of a pixel, and Apix=Dpix$^2$=2.5×10$^{-3}$ cm$^2$ is the area of the pixel. The pencil beam cross-sectional area is twice the area of a pixel because the Nyquist Theorem applies in the scan direction. The pencil beam cross-section is a rectangle where the dimension along the line scan is twice the dimension perpendicular to the line scan.

The size of the projected x-ray source in the tumor, Dprojx, due to the demagnification of the x-ray source diameter is the diameter of the x-ray source, Dx, times the ratio of the distance from the pinhole to the soft tissue, dphtumor, divided by the distance from the pin hole to the source, Dphsource. If Dx=0.04 cm, dphtumor=2.7 cm, and Dphsource=15 cm, then Dprojx=Dx×(dphtumor/Dphsource)=7.2×10-3 cm, so the pencil beam width of 1 mm is not made larger due to the source size.

The solid angle subtended by the backscatter detector at an average location in the tumor, $\Omega$det, is calculated below. a and b are the lateral y and x dimensions, respectively, of the flat backscatter detector and z is the perpendicular distance 52 from a point 8 in the tumor 4 to the face 50 of the scintillator 42, as shown in FIG. 1. The worst case is calculated where the center of the tumor 4 is furthest away from edge of the hole 44 in the scintillator 42. Assuming that an index, i=0 . . . 20 (corresponding to 21 different skin depths), the square opening 44 in the scintillator 42 size is 2.5 cm×2.5 cm, the total area of the scintillator 42 (with the square opening 44 in the center) is a x b=5 cm×5 cm=25 cm$^2$, and z=varies from 0 cm to 2 cm, then $$\Omega\text{det}_i := 4 \cdot \left[ \int_0^a \int_0^b \frac{z_i}{[x^2 + y^2 + (z_i)^2]^{\frac{3}{2}}} dx\,dy - \int_0^{1.25} \int_0^{1.25} \frac{z_i}{[x^2 + y^2 + (z_i)^2]^{\frac{3}{2}}} dx\,dy \right]$$

Figure 3:
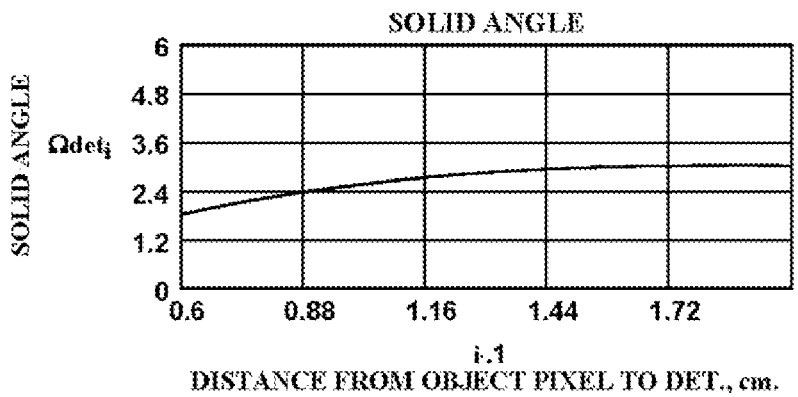
FIG. 3 is a graph of the solid angle, in steradians, subtended by the plastic backscatter detector as a function of the distance along the pencil beam of x-rays where the pencil beam produces backscatter x-rays.

FIG. 3 shows the solid angle, in steradians, as a function of z, the distance from the origin of the backscattered x-ray to the underside of the backscatter detector.

After performing the above calculation, it is determined that the total average solid angle is 2.5 steradians.

Figure 4:
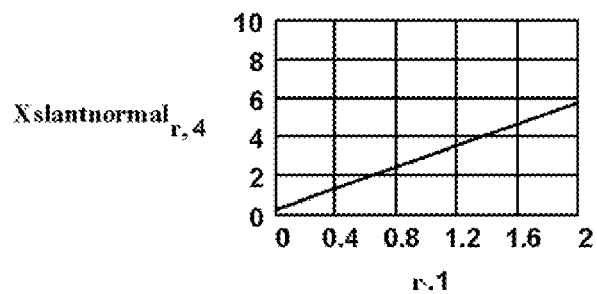
FIG. 4 is a graph of the slant distance that the backscattered x-rays must traverse versus the corresponding normal distance of the incident pencil beam.

The total solid angle subtended by the detector at the scattering voxel is about 2.5 steradians. This solid angle is divided into five equal portions, $\Omega$fix, each of the same size, and the distance Xrs from this voxel along the corresponding slant angle of the solid angle up to the surface of the backscatter detector is measured. $\Theta$s is the slant angle between the normal to the surface and the line from the voxel to the surface for the particular solid angle defined by s. Assume then that $\Omega$tot=2.5, $\Omega$fix=($\Omega$tot)/5, s=0 . . . 4, and $\Theta$s=a cos [1−(s× $\Omega$fix)/2$\pi$). The distance to the surface, Xslant, is shown below. The thickness, in g/cm$^2$, used in the calculation is denstumor=1+0.005 and index r=0 . . . 20. If Xnormal$_r$=0.1+ 0.1×r and Xtumor$_r$=Xnormal$_r$×denstumor g/cm$^2$, then Xslantnormal$_{r,s}$=Xnormal$_r$/cos($\Theta$s) g/cm$^2$ and Xslanttumor$_{r,s}$=Xtumor$_r$/cos($\Theta$s) g/cm$^2$. A graph showing Xslantnormal versus r is shown in FIG. 4.

Figure 5:
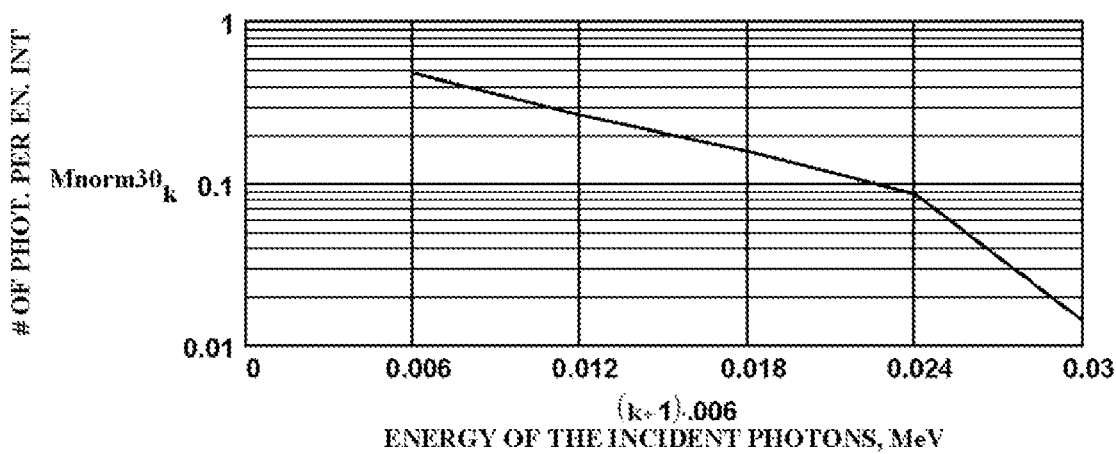
FIG. 5 is a graph of the normalized energy spectrum of the incident pencil beam.

The matrices below show a typical photon spectrum of the x-ray source. The first column is the relative number of photons in the energy interval of 6 keV for the 30 keV x-ray source and 14 keV for the 70 keV source and the second column shows the energy in MeV. k=0 . . . 4 and m=0 . . . 1.

$$M30 := \begin{pmatrix} 1 & .006 \\ .55 & .012 \\ .33 & .018 \\ .18 & .024 \\ .03 & .030 \end{pmatrix}$$

$$M70 := \begin{pmatrix} 1 & .014 \\ .55 & .028 \\ .33 & .042 \\ .18 & .056 \\ .03 & .070 \end{pmatrix}$$

$$\mu tis30 := \begin{pmatrix} 6 & 20 \\ 12 & 3.1 \\ 18 & 1.0 \\ 24 & .36 \\ 30 & .16 \end{pmatrix}$$

$$\mu tis70 := \begin{pmatrix} 14 & 2.1 \\ 28 & .169 \\ 42 & .084 \\ 56 & .037 \\ 70 & .029 \end{pmatrix}$$

$$Mnorm70_k := \frac{M70_{k,0}}{\sum_k M70_{k,0}} \quad Mnorm30_k := \frac{M30_{k,0}}{\sum_k M30_{k,0}} \quad \sum_k Mnorm30_k = 1$$

where Mnorm is the normalized spectrum of the incident photons. FIG. 5 is a graph of the result for $Mnorm30_k$. This graph shows the normalized energy spectrum for the 30 keV peak energy source.

The power output of the x-ray tube is taken to be 30 watts. For each embodiment of the invention, the minimum required power output is determined by the calculation of the number of photons required to achieve the desired contrast in the x-ray image. This power is always less than in the prior art. The x-ray source to tumor distance in this embodiment is 18 cm. This distance can be made smaller, which would require even less power from the x-ray source. The time of exposure is 2 seconds.

The hole in the template moves rapidly in the x direction a distance of 2.5 cm back and forth. In the y direction, the pencil beam moves a distance of one pinhole width, Dpix, while the pencil beam moves 2.5 cm in the x direction. Assume that the total time for an exposure of the patient, Ty, is 2 seconds and the time for a single x traversal is Tx. If the number of x traversals is 2.5/Dpix=2.5/0.05=50, then Tx=(Ty×Dpix)/2.5, or Tx=0.04 sec, and the velocity in the x direction, Vx, is 2.5/Tx=62.5 cm/sec. This is slow enough to use the desired stepping or servo motors. The sample time per pixel is therefore 2/(50×50)=0.0008 sec or 0.8 msec.

The measured radiation exposure, R Roentgens/mA/min, can be found in ICRP (1960), in R/mA/min at 1 meter from target. The matrix below shows the radiation output of a typical x-ray tube as a function of the peak x-ray voltage. The first column is the peak x-ray voltage in keV. The second column is the corresponding output in R/mA/min at 1 meter from the target.

$$Roentgen := \begin{pmatrix} 20 & .2 \\ 40 & .375 \\ 60 & .61 \\ 80 & .9 \\ 100 & 1.09 \\ 120 & 1.48 \\ 140 & 2 \\ 160 & 2.31 \\ 180 & 2.78 \\ 200 & 3 \end{pmatrix}$$

For a tube operating at 30 keV peak, the above matrix is interpolated to arrive at an output per minute of 0.2875 R/mA/min, which is converted to output per second Roentgen30 mA=0.2875/60=4.792×10$^{-3}$ R/sec/mA at 1 meter. It is converted into output per watt, as follows: Vtube30=30×10$^{-3}$ eV, so Itube30=(Wtube30/Vtub30)×10$^3$ mA. Thus the output from the x-ray tube operating at 30 keV peak and with the dimensions of the system, is as follows:

$$Roentgen30\ W := Roentgen30\ mA \cdot \left(\frac{100}{15}\right)^2 \cdot \left(\frac{Wtube30}{Vtube30} \cdot 10^3\right) \cdot 2 *$$

Similarly, for the tube operating at 70 keV peak:

$$Vtube70 := 70 \cdot 10^3 *$$

$$Roentgen70\ mA := \frac{.755}{60}\ \text{R/sec/mA at 1 meter}$$

$$Itube70 := \frac{Wtube70}{Vtube70} \cdot 10^3 *$$

$$Roentgen70\ W := Roentgen70\ mA \cdot \left(\frac{100}{15}\right)^2 \cdot \left(\frac{Wtube70}{Vtube70} \cdot 10^3\right) \cdot 2$$

$$Rtemp70 := Roentgen70\ mA \cdot \left(\frac{100}{15}\right)^2 \cdot \left(\frac{Wtube70}{Vtube70} \cdot 10^3\right) \cdot 2 *$$

The amount of roentgens at the template 15 cm from the source and with a time of exposure of 2 seconds is Rtemp30=0.426 R and Rtemp70=0.479 R.

The corresponding x-ray flux at 1 meter, R/meter, is $$Nphot30_k := \frac{Rtemp30 \cdot 2.15 \cdot 10^9}{M30_{k,1}} \cdot Mnorm30_k$$

$$Nphot70_k := \frac{Rtemp70 \cdot 2.15 \cdot 10^9}{M70_{k,1}} \cdot Mnorm70_k$$

Figure 6:
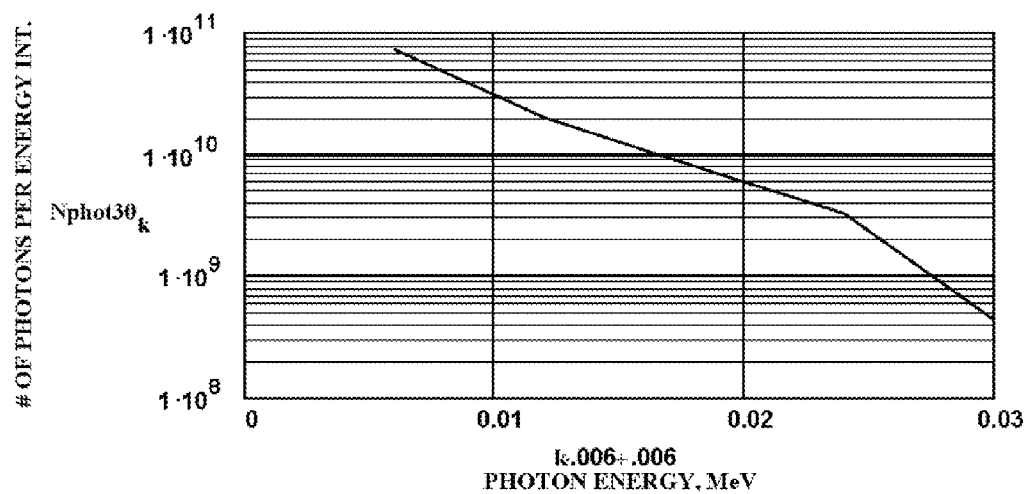
FIG. 6 is a graph of the number of photons per energy interval for the x-ray source of 30 keV peak energy.
Figure 7:
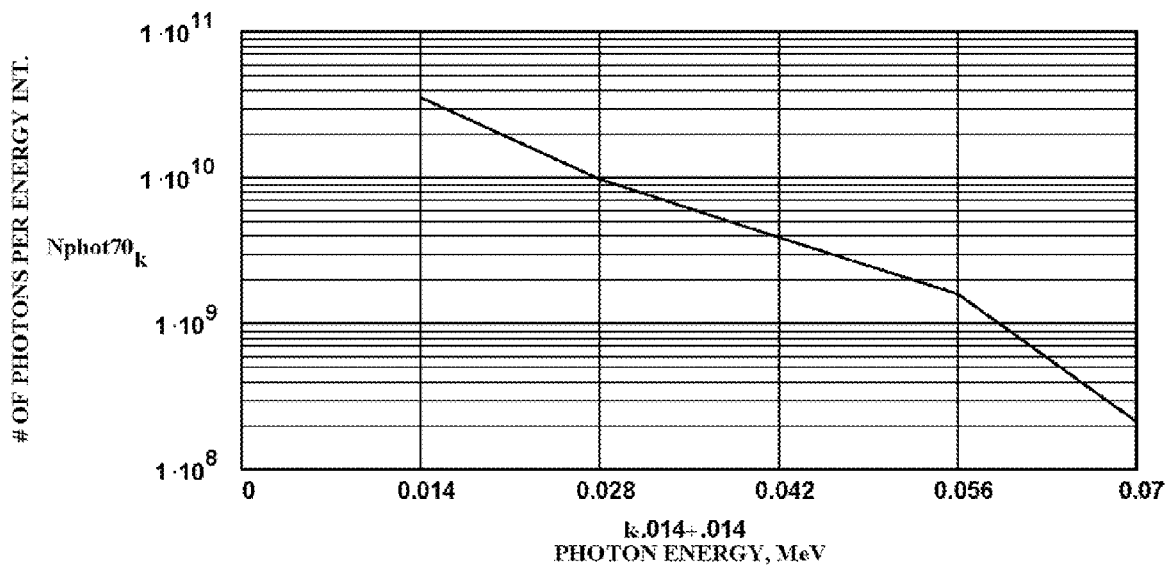
FIG. 7 is a graph of the number of photons per energy interval for the x-ray source of 70 keV peak energy.

Graphs showing the solution to the above equations are shown in FIG. 6 for the 30 keV x-ray source and in FIG. 7 for the 70 keV x-ray source.

Apen=4×Apix cm$^2$ is the area of the pencil beam, which is four times the area of a pixel as the Nyquist Theorem is applied. If Apix=2.5×10$^{-3}$ cm$^2$, then Apen=0.01 cm$^2$.

Assume that Rtemp is the exposure to the total target area, the total target area is 2.5 cm×2.5 cm, and the distance from the source to the template is 15 cm. Rpb is the flux delivered to the target area. Rpb30=Rtemp30(Apen/2.5$^2$)=6.815×10$^{-4}$ R and Rpb70=Rtemp70(Apen/2.5$^2$)=7.67×10$^{-4}$ R.

The number of photons per sample, Nphotsample30k=Apen×Nphot30k photons incident/pencil beam/sample/energy interval and Nphotsample70k=Apen×Nphot70k photons incident/pencil beam/sample/energy interval. The total number of photons per pencil beam, Nphottot is $$Nphototot30 := \sum_k Nphotsample30_k \quad Nphototot30 = 1.049 \times 10^9$$

$$Nphototot70 := \sum_k Nphotsample70_k \quad Nphototot70 = 5.058 \times 10^8$$

and the number of photons that reaches the depth X, without interaction is Npb:

$$Npbnormal30_{k,r} := [Nphotsample30_k \cdot e^{-(Xnormal_r)\cdot(\mu tis30_{k,1})}]$$

$$Npbtumor30_{k,r} := [Nphotsample30_k \cdot e^{-(Xtumor_r)\cdot(\mu tis30_{k,1})}]$$

$$Npbnormal70_{k,r} := [Nphotsample70_k \cdot e^{-(Xnormal_r)\cdot(\mu tis70_{k,1})}]$$

$$Npbtumor70_{k,r} := [Nphotsample70_k \cdot e^{-(Xtumor_r)\cdot(\mu tis70_{k,1})}]$$

Now the number of photons that are scattered backwards into the backscatter detectors is calculated. Assume that the backscattered photons are scattered backwards by an angle of 180°±about 30°. The American Institute of Physics (AIP) Handbook has the relevant differential cross-sections, μe, in steradians per electron as a function of angle and incident photon energy. It is shown there that μe is constant over the relevant angles to a good approximation for each of the photon energies of interest. The AIP Handbook also lists the energy of the backscattered photon as a function of the energy of the incident photon and the angle of the backscattered photon. There is little change in energy of the scattered photon for any of the energies of the x-rays that are relevant to the present calculation.

$$\mu e30 := \begin{pmatrix} 6 & 68 \\ 12 & 64 \\ 18 & 58 \\ 24 & 56 \\ 30 & 52 \end{pmatrix} \cdot 10^{-27} \quad \mu e70 := \begin{pmatrix} 14 & 62 \\ 28 & 54 \\ 42 & 52 \\ 56 & 46 \\ 70 & 40 \end{pmatrix} \cdot 10^{-27}$$

where column 1 is the energy of the incident photon and column 2 is the cross-section for backscatter of the incident photon in (cm²/electron).

$$\mu bstis30 := \begin{pmatrix} 6 & 24 \\ 12 & 3 \\ 18 & 1 \\ 24 & .45 \\ 30 & .16 \end{pmatrix} \quad \mu bstis70 := \begin{pmatrix} 14 & 1.6 \\ 28 & .18 \\ 42 & .06 \\ 56 & .038 \\ 70 & .030 \end{pmatrix}$$

where column 1 is the energy of the incident photon (keV) and column 2 is the mass absorption coefficient of the backscattered x-rays on their way out of the soft tissue.

The number of photons scattered into the backscatter detector from the soft tissue with no tumor after the incident beam has traversed a thickness of X in the sample is Nback30 or Nback70. eff=0.6 is the efficiency of the backscatter detector in detecting single photons.

$$Nbacknormal30_r := \sum_k Npbnormal30_{k,r} \cdot$$

$$\Omega fix \cdot .1 \cdot \mu e30_{k,1} \cdot eff \cdot Ne \cdot \sum_{s=0}^{4} e^{(-Xslantnormal_{r,s})\cdot(\mu bstis30_{k,1})}$$

$$Nbacktumor30_r := \sum_k Npbtumor30_{k,r} \cdot$$

$$\Omega fix \cdot .1 \cdot \mu e30_{k,1} \cdot eff \cdot Ne \cdot \sum_{s=0}^{4} e^{(-Xslanttumor_{r,s})\cdot(\mu bstis30_{k,1})}$$

$$Nbacknormal30total := \sum_r Nbacknormal30_r \quad Nbacktumor30total :=$$

$$\sum_r Nbacktumor30_r$$

Nbacknormal30total=2.334×10⁶
Nbacktumor30total=2.322×10⁶

$$SDNbacknormal30total := \sqrt{Nbacknormal30total}$$

$$\Delta 30total := Nbacknormal30total - Nbacktumor30total$$

$$SD\Delta 30total := \sqrt{Nbacknormal30total + Nbacktumor30total}$$

$$Nbacknormal70_r := \sum_k Npbnormal70_{k,r} \cdot$$

$$\Omega fix \cdot .1 \cdot \mu e70_{k,1} \cdot eff \cdot Ne \cdot \sum_{s=0}^{4} e^{-Xslantnormal_{r,s}\cdot(\mu bstis70_{k,1})}$$

$$Nbacktumor70_r := \sum_k Npbtumor70_{k,r} \cdot$$

$$\Omega fix \cdot .1 \cdot \mu e70_{k,1} \cdot eff \cdot Ne \cdot \sum_{s=0}^{4} e^{-Xslanttumor_{r,s}\cdot(\mu bstis70_{k,1})}$$

$$Nbacknormal70total := \sum_r Nbacknormal70_r \quad Nbacktumor70total :=$$

$$\sum_r Nbacktumor70_r$$

Nbacknormal70total=7.497×10⁶
Nbacktumor70total=7.477×10⁶

$$SDNbacknormal70total := \sqrt{Nbacknormal70total}$$

$$\Delta 70total := Nbacknormal70total - Nbacktumor70total$$

$$SD\Delta 70total := \sqrt{Nbacknormal70total + Nbacktumor70total}$$

After performing the above calculations, it is found that SDΔ30total=2.158×10³ photons/pixel and SDΔ70total=3.87×10³ photons/pixel.

If nSΔ is the number of standard deviations (SDs) per pixel between the tumor tissue and the normal tissue, then nSΔ30=Δ30total/SDΔ30total=5.457 SDs and
nSΔ70=Δ70total/SDΔ70total=5.041 SDs.

In summary, for an x-ray tube operating at 30 keV peak and 30 watts of power, an assumed difference in density between tumor tissue and normal tissue of 0.5%, an examination time of 2 sec for a 2.5 cm×2.5 cm skin area, a pixel size of 0.5 mm, an assumed maximum depth of the tumor from the surface of 2 cm, the contrast between tumor tissue and normal tissue is about 5 standard deviations per pixel.

Figure 8:
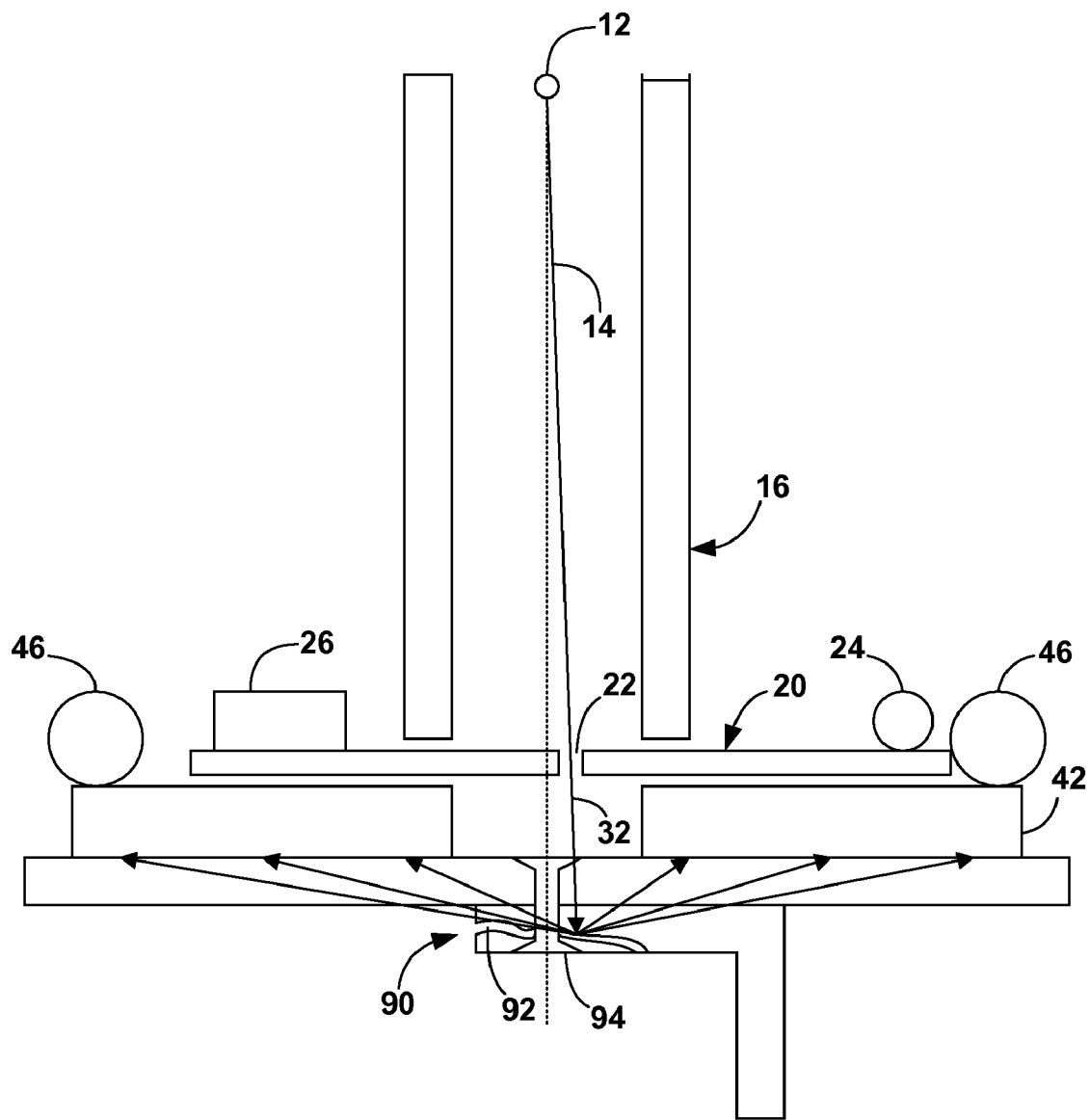
FIG. 8 is a schematic side view of another embodiment of the present invention.

FIG. 8 shows another application of the present invention. A major problem with aging aircraft is the failure of wings and tail structures due to fatigue, resulting in aircraft accidents. There are many systems in place to inspect aircraft for the existence of fatigue cracks around rivets, and the Federal Aviation Administration is very concerned about this problem with a branch dedicated to the problem. Ultrasound imaging is employed by numerous prior art systems. In addition, a company, YXlon, offered a crude backscatter system that did not use a single large area detector, but instead used a broad area incident beam and an array of focused detectors that each saw a tiny portion of the scatter from the broad area incident beam of x-rays.

The present invention is particularly effective in detecting fatigue cracks 92 in aircraft structures 90, for example, around rivets 94, because of its sensitivity to the sudden changes in density characteristic of these cracks 92. The system of the present invention is orders of magnitude more efficient at detecting fatigue cracks than the YXlon system.

Detecting cracks is somewhat easier than detecting tumors because the change in density between the air in the crack 92 and the metal 90 of the aircraft is very large. On the other hand, the crack 92 may be of small width, so the pinhole 22 must be made smaller. These two things compensate one another.

Figure 9:
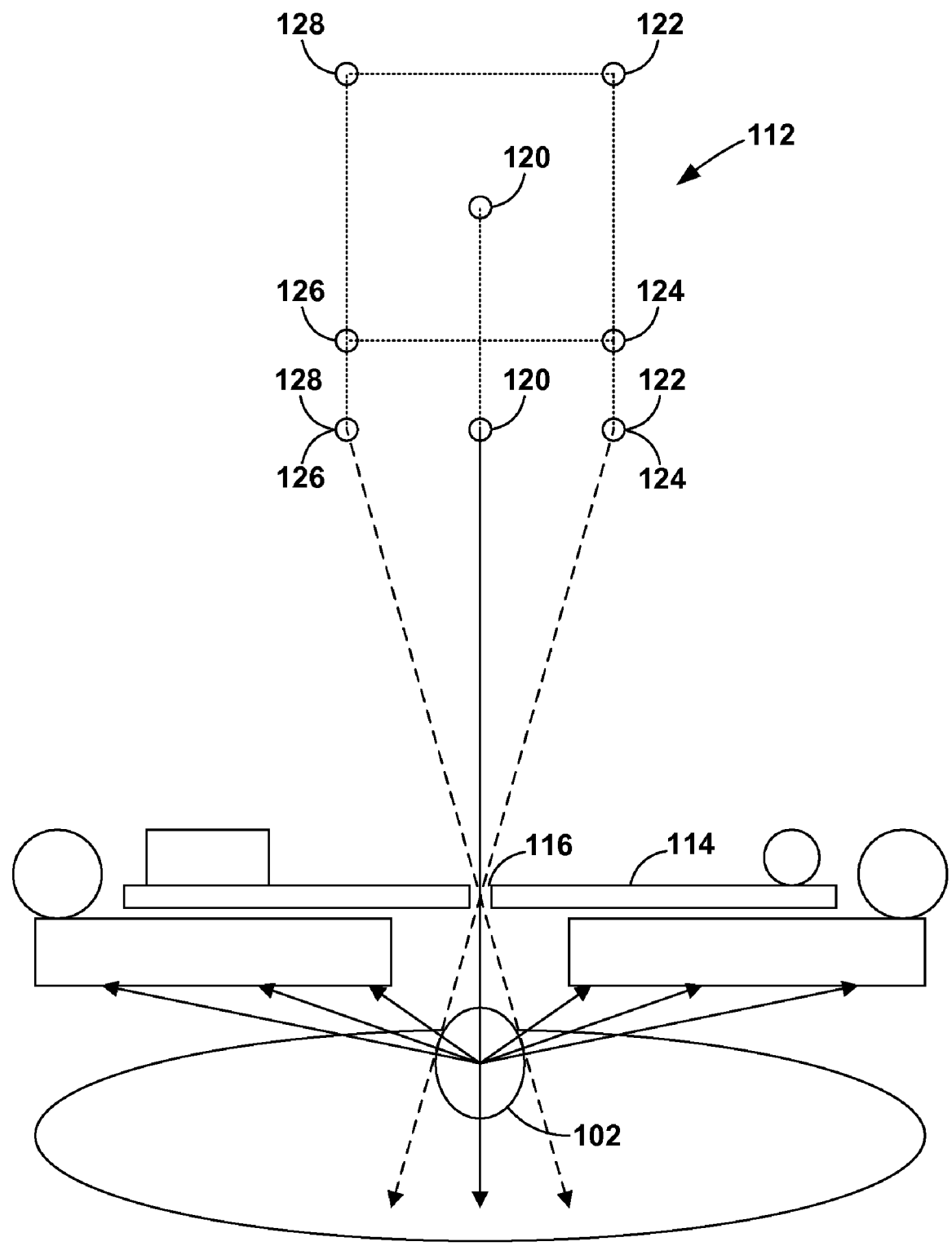
FIG. 9 is a schematic side view of yet another embodiment of the present invention.
Figure 10:
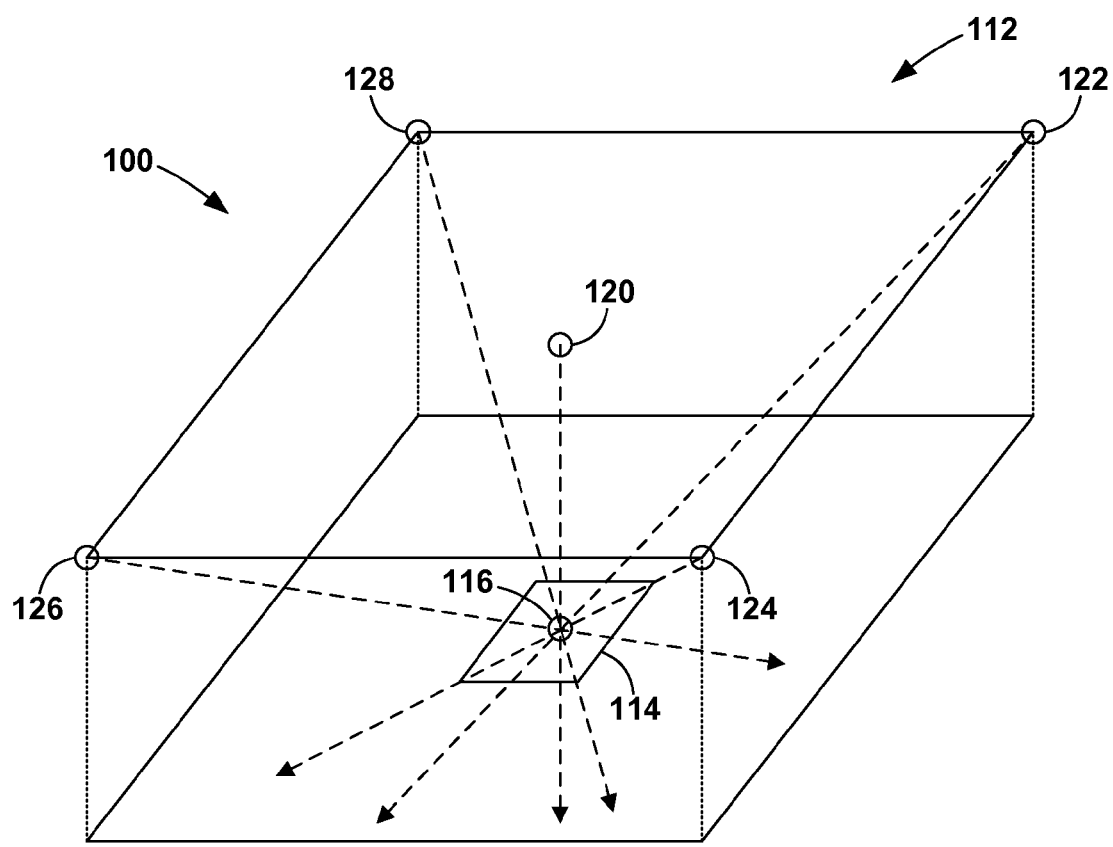
FIG. 10 is an isometric view of a portion of the embodiment of FIG. 9.

FIGS. 9 and 10 show an embodiment 100 of the present invention that can be used to produce 3D tomography images. To produce a 3D tomography image, the method described above to produce a single image of the target region is performed a plurality of times, with the x-ray source 112 in a different location relative to the pinhole 116 for each image. FIGS. 9 and 10 show an example of five different locations 120, 122, 124, 126, 128 for the x-ray source 112, where the center location 120 is the same as described above. FIG. 10 shows an isometric view of the five locations 120, 122, 124, 126, 128 for the x-ray source 112. FIGS. 9 and 10 show all of the locations in a single plane parallel to the template 114, but the present invention is not limited to this configuration. The x-ray source locations may be in a plane that is not parallel to the template. They may be in a single line that is or is not parallel to the template. They may be at random locations and not planar or linear at all. The number of x-ray source locations can vary depending upon the image clarity desired and can be three source locations or more.

In one embodiment, each x-ray source location has an independent x-ray source. In another embodiment, a single x-ray source is moved among the different x-ray source locations.

With the example configuration of FIGS. 9 and 10, five backscatter images are produced of the target region 102. These five images are combined to produce digital tomography images of "slices" parallel to the surface of the target region 102 at different depths within the target region 102 being scanned. The combining algorithm may be one of several well-known algorithms used to combine multiple transmission images.

This invention is the first known practical method of producing 3D digital tomography images that uses blurring in two orthogonal directions. All prior art systems move the x-ray source substantially in a plane perpendicular to the surface of the object and/or in a straight line or an arc of a circle. Blurring in two orthogonal directions removes many of the artifacts found in all prior art systems.

Thus it has been shown and described a x-ray backscatter system for imaging at shallow depths which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. An apparatus for x-ray imaging of a target region of an object at shallow depths comprising:
    (a) an x-ray source generating a cone beam at least one peak voltage in the range of from approximately 10 keV to approximately 500 keV;
    (b) a planar template receiving said cone beam, said template in the range of from approximately 2.5 cm to approximately 30 cm from said source, said template having a pinhole with a width and an area in the range of from approximately 0.01 mm$^2$ to approximately 4 mm$^2$, said template passing only said x-rays impinging on said pinhole as a pencil beam;
    (c) means for moving said template in the plane of said template in increments of approximately one half of said pinhole width so as to scan said target region with a spatial resolution of one half of said pinhole width; and
    (d) a detector having a scintillator with a thickness in the range of from approximately 0.5 mm to approximately 3 cm, said scintillator having an opening through which said pencil beam passes to said target region, said scintillator being adapted to be located adjacent to said target region;
    (e) whereby, as said pencil beam scans said target region, backscatter x-rays from said target region are received by said scintillator, which are used to form images of said target region.

2. The apparatus of claim 1 wherein said scintillator is fixed relative to said x-ray source and said opening is approximately the size of said target region.

3. The apparatus of claim 1 wherein said scintillator is fixed relative to said template such that said scintillator moves with said template, and said scintillator opening is slightly larger than said pinhole.

4. The apparatus of claim 1 further comprising a guide between said source and said template.

5. The apparatus of claim 1 wherein said means for moving said template include stepping or servo motors.

6. The method of claim 1 wherein said x-ray source emits x-rays at multiple peak voltages and said images are compared to derive information about the atomic or molecular composition or density of the material in said target region.

7. A method for x-ray imaging a target region of an object at shallow depths comprising the steps of:
    (a) providing, in the following order, an x-ray source, a planar template having a pinhole having an area in the range of from approximately 0.01 mm$^2$ to approximately 4 mm$^2$, and a detector assembly with a scintillator parallel to said template and having a thickness in the range of from approximately 0.5 mm to approximately 3 cm, said scintillator being adapted to be located adjacent to said target region;

(b) said x-ray source emitting an x-ray cone beam to said template at least one peak voltage in the range of from approximately 10 keV to approximately 500 keV, (c) said template blocking said x-ray cone beam except at said pinhole, said pinhole passing said x-ray cone beam as a pencil beam;

(d) said pencil beam passing through an opening in said scintillator and impinging on said target region;

(e) moving said template in the plane of said template such that said pencil beam scans said target region;

(f) said scintillator receiving backscatter x-rays from said target region; and (g) forming images of said target region from said backscatter x-rays.

8. The method of claim 7 wherein a guide between said source and said template is provided.

9. The method of claim 7 wherein said scintillator is fixed relative to said x-ray source and said opening is approximately the size of said target region.

10. The method of claim 7 wherein said scintillator is fixed relative to said template such that said scintillator moves with said template, and said scintillator opening is slightly larger than said pinhole.

11. The method of claim 7 wherein said x-ray source emits x-rays at multiple peak voltages and said images are compared to derive information about the atomic or molecular composition or density of the material in said target region.

12. A method for x-ray imaging a target region of an object at shallow depths comprising the steps of:

(a) providing, in the following order, at least three x-ray sources at different locations, a planar template having a pinhole having an area in the range of from approximately 0.01 mm² to approximately 4 mm², and a detector assembly with a scintillator parallel to said template and having a thickness in the range of from approximately 0.5 mm to approximately 3 cm, said scintillator being adapted to be located adjacent to said target region;

(b) each of said x-ray sources emitting x-ray cone beams successively to said template at least one peak voltage in the range of from approximately 10 keV to approximately 500 keV;

(c) said template blocking each of said x-ray cone beams except at said pinhole, said pinhole passing each of said x-ray cone beams as a pencil beam;

(d) each of said pencil beams passing through an opening in said scintillator sheet and impinging on said target region;

(e) moving said template in the plane of said template such that each of said pencil beams scans said target region;

(f) said scintillator receiving backscatter x-rays from said target region; and (g) forming images of said target region from said backscatter x-rays from said x-ray sources.

13. The method of claim 12 wherein said opening is approximately the same size as said target region.

14. The method of claim 12 wherein said scintillator is fixed relative to said template such that said scintillator moves with said template, and said scintillator opening is slightly larger than said pinhole.

15. The method of claim 12 wherein said x-ray sources are located along a line.

16. The method of claim 12 wherein said x-ray sources are located along a line parallel to said template.

17. The method of claim 12 wherein said x-ray sources are located in a plane parallel to said template.

18. The method of claim 12 wherein the images are combined to produce a three-dimensional digital tomography image of the volume of said target region.

19. The method of claim 12 wherein said x-ray sources emit x-rays at multiple peak voltages and said images are compared to derive information about the atomic or molecular composition or density of the material in said target region.

* * * * *